(12) United States Patent
Lindquist

(10) Patent No.: US 7,967,602 B2
(45) Date of Patent: Jun. 28, 2011

(54) PLIERS FOR FORMING ORTHODONTIC WIRES

(76) Inventor: John Theodore Lindquist, Indianapolis, IN (US)

(*) Notice: Subject to any disclaimer, the term of this patent is extended or adjusted under 35 U.S.C. 154(b) by 302 days.

(21) Appl. No.: 12/246,662

(22) Filed: Oct. 7, 2008

(65) Prior Publication Data

US 2010/0086889 A1  Apr. 8, 2010

(51) Int. Cl.
*A61C 7/04* (2006.01)
(52) U.S. Cl. ............ 433/4; 433/159; 81/416; 72/409.1; 140/106
(58) Field of Classification Search ............. 433/4, 159; 81/3.6, 319, 328, 352, 354, 424.5, 416, 318, 81/320; 72/409.1; 140/104, 106; 606/205–208
See application file for complete search history.

(56) References Cited

U.S. PATENT DOCUMENTS

| | | | |
|---|---|---|---|
| 2,501 A * | 3/1842 | Wendt | 30/261 |
| 967,436 A * | 8/1910 | Ramsey | 30/267 |
| 1,103,606 A | 7/1914 | Montag | |
| 1,108,493 A | 8/1914 | Federspiel | |
| 1,111,110 A * | 9/1914 | Trost | 72/409.16 |
| 1,510,416 A * | 9/1924 | Pietz et al. | 606/205 |
| 1,517,162 A * | 11/1924 | King | 81/339 |
| 1,619,084 A | 3/1927 | Miller | |
| 2,274,945 A * | 3/1942 | Van Keuren | 7/134 |
| 2,396,619 A * | 3/1946 | Strayer | 72/31.05 |
| 2,704,399 A * | 3/1955 | Melcher | 30/266 |
| 2,741,843 A * | 4/1956 | Sejman et al. | 30/266 |
| 2,755,692 A * | 7/1956 | Wallshein | 72/390.5 |
| 2,954,606 A | 10/1960 | Peak | |
| 3,146,804 A * | 9/1964 | Wallshein | 140/106 |
| 3,170,237 A | 2/1965 | Weidauer | |
| 3,244,201 A * | 4/1966 | Wallshein | 140/106 |
| 3,421,553 A | 1/1969 | Redmon | |
| 3,429,173 A * | 2/1969 | Waddell | 72/409.12 |
| 3,507,043 A * | 4/1970 | Rubin | 433/4 |
| 3,650,028 A * | 3/1972 | La Pointe | 30/238 |
| 3,727,316 A * | 4/1973 | Goldberg | 433/4 |
| 3,735,763 A * | 5/1973 | Shannon et al. | 606/208 |
| 3,774,306 A * | 11/1973 | Dobyns | 433/4 |
| 3,804,132 A * | 4/1974 | Mann | 140/106 |
| 4,038,755 A * | 8/1977 | Hernandez | 433/4 |
| 4,184,259 A * | 1/1980 | Sosnay | 433/4 |
| 4,630,462 A | 12/1986 | Wiener et al. | |
| 4,693,246 A | 9/1987 | Reimels | |
| 5,084,935 A | 2/1992 | Kalthoff | |
| 5,220,856 A | 6/1993 | Eggert et al. | |
| 5,395,236 A | 3/1995 | Khouri | |
| 5,865,075 A | 2/1999 | Medved | |
| 6,293,791 B1 | 9/2001 | Weinstein | |
| 7,258,047 B1 | 8/2007 | Wolter et al. | |
| 7,318,725 B2 * | 1/2008 | Zepf | 433/159 |
| 2002/0146665 A1 * | 10/2002 | Tamura | 433/159 |
| 2003/0079576 A1 * | 5/2003 | Lo | 81/318 |
| 2006/0259072 A1 * | 11/2006 | Di Emidio | 606/205 |
| 2008/0153051 A1 | 6/2008 | Hart et al. | |

* cited by examiner (Continued)

*Primary Examiner* — Todd E Manahan
*Assistant Examiner* — Michael R Ballinger
(74) *Attorney, Agent, or Firm* — Dorr, Carson & Birney, P.C.

(57) ABSTRACT

A pliers for forming orthodontic wires has opposing beaks with complementary wire-forming surfaces that include interfering portions. A hinge mechanism enables the beaks to open and close by rotating about an axis, and also allows a range of axial motion between the beaks sufficient to prevent interference between the wire-forming surfaces as the beaks are closed. By preventing such interference, novel over-bending capabilities can be achieved to form useful bending of low spring rate wire. A spring, such as a Belleville washer, exerts a biasing force parallel to the hinge axis to maintain alignment of the beaks, but allows the required range of axial motion between the beaks to prevent interference.

18 Claims, 10 Drawing Sheets

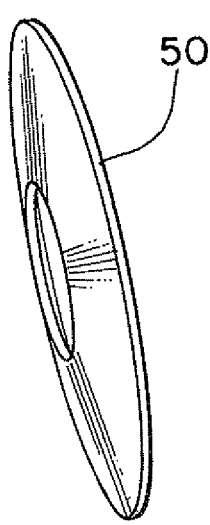
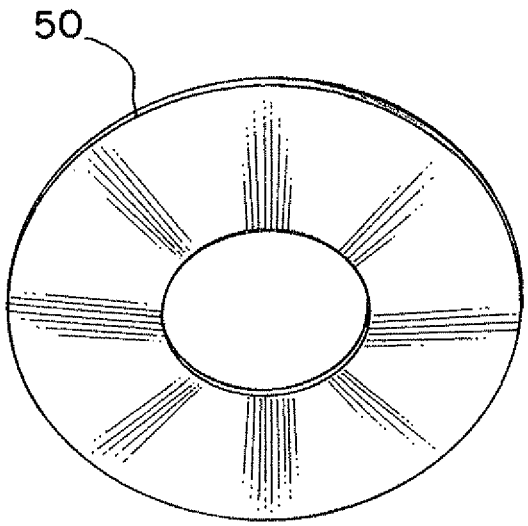
*Fig. 6*  *Fig. 7*
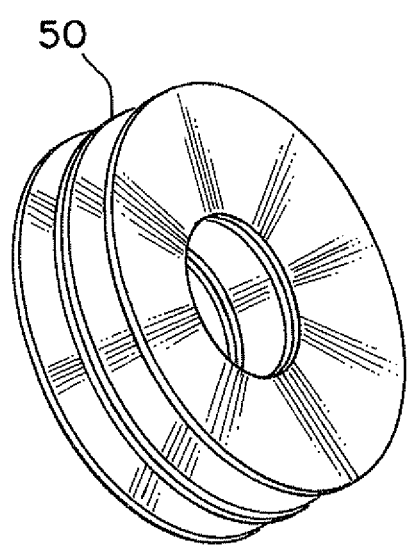
*Fig. 8*

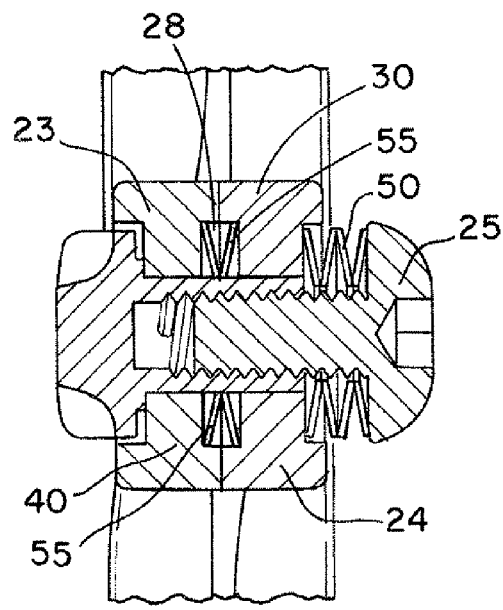 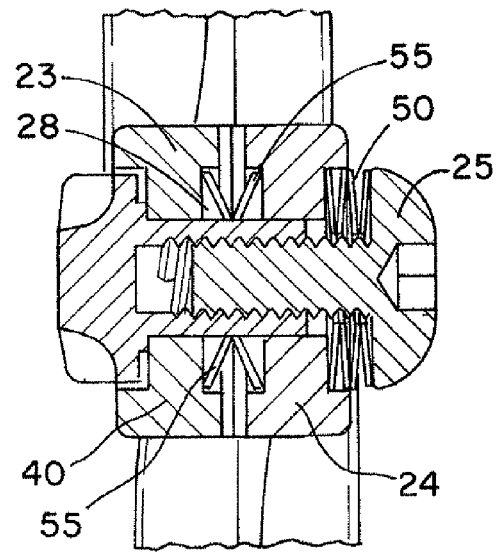
*Fig. 13a*     *Fig. 13b*
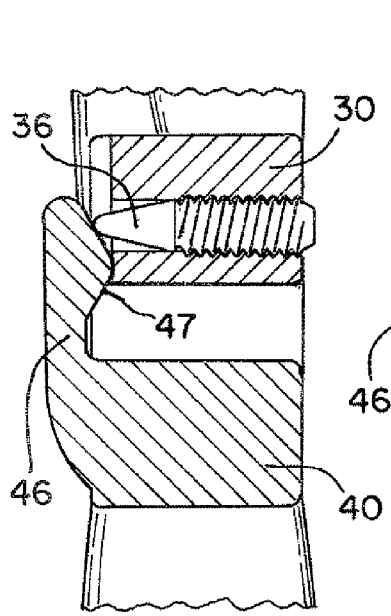 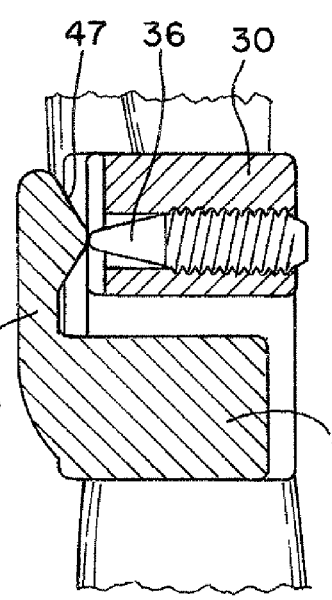 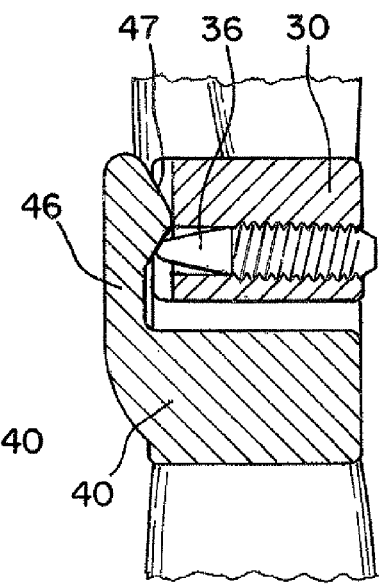
*Fig. 14a*     *Fig. 14b*     *Fig. 14c*

PLIERS FOR FORMING ORTHODONTIC WIRES

BACKGROUND OF THE INVENTION

1. Field of the Invention

The present invention involves the dental specialty of orthodontics and in particular, an improved instrument used to form orthodontic wires.

2. Statement of the Problem

In the broadest sense, the practice of orthodontics can be reduced to the steps of directing carefully regulated corrective forces onto individual teeth. Such forces are typically generated by various types of energy-storing springs that initiate and then maintain the physiological processes supporting tooth movement. The current orthodontic armamentarium includes many configurations of such energy-storing springs, many of which have been developed for specific but common challenges facing orthodontists. The most common energy-storing spring used in nearly all orthodontic treatment methodologies is the archwire. Archwires are formed in the familiar U-shape of the human dental arch. Such wires normally extend around the front of the arch from molar to molar. Archwires provide the prime tooth-moving motive force and provide the continuity of forces around the arch. Archwires generate forces that span multiple teeth such as leveling, arch development (expansion) and transverse expansion, and have the capability of anchoring all of the teeth of one arch in apposition to the other arch for anterior-posterior correction of the entire occlusion.

In practice, devices known as orthodontic brackets are rigidly attached to each tooth of an arch. Brackets feature a horizontally oriented and labially or buccally opening slot that serves to accept and engage an archwire. Once the archwire is inserted into a bracket's arch slot, it is retained therein by ligatures that engage tie-wings of the bracket. U.S. Pat. No. 3,504,438 to Wittman et al. discloses orthodontic brackets with arch slots and an archwire in place.

Arch slots are defined by two parallel slot walls and a slot floor that is oriented perpendicular to the walls. Within the orthodontic profession, standards for arch slot dimensions have been established. According to those standards, an arch slot width may be about 0.018 inches or 0.022 inches wide and about 0.028 or 0.030 in. deep. As can be appreciated then, the arch slot in cross-section can be thought of as being rectangular, but with one side of the rectangle open to allow the archwire to be inserted.

Being rectangular in cross-section, arch slots can accept appropriately-sized square and rectangular archwires as well as round archwires. It is the relationship between square and rectangular wire and rectangular arch slots that is of particular importance in orthodontics. When an archwire is formed from rectangular wire, for example, and provided the dimensions of its rectangular profile closely coincide with the dimensions of the receiving arch slot, torsional forces can be transferred from the archwire to the bracket when the two are engaged. In contrast, a round archwire is generally incapable of transferring torque in this manner.

Such torsional forces are ultimately transferred to the tooth root and the supporting bone, and allow the tooth to reposition over time. Correction of undesirably lingually or labially-inclined teeth is typically accomplished by corrective forces in terms of torque. Torque, along with other force vectors referred to as angulation, rotation, intrusion and extrusion, bodily movement and translation along an archwire are types of corrective forces that are transferred to teeth by an archwire. Torque in particular however requires the rectangular relationship between the archwire and its receiving slot in the bracket.

The mechanical relationship between a rectangular wire and a bracket's rectangular arch slot, and the orthodontic methods that employ that relationship are known as "Edgewise Mechanics". The principles of Edgewise mechanics were introduced in the early 1900's but still play a central role in the practice of orthodontics today.

Over the course of treatment, orthodontic archwires must exhibit a wide range of mechanical properties to accommodate the changing force requirements of progressive phases of treatment. For example, teeth tend to be chaotically positioned and well out of alignment at the beginning of treatment. As orthodontic treatment begins, the arch slots of the brackets attached to these teeth will be similarly be chaotically-oriented relative to each other. An archwire ligated into such an array of mal-aligned arch slots must be capable of accommodating sharp bends, turns and twists without taking a set, while at the same time exerting gentle, safe, and continuous corrective forces to the teeth. In other words, archwires used at the beginning of treatment must exhibit a low spring rate at high deflection.

At a midpoint in treatment, the teeth and the arch slots attached to them will have responded to treatment by repositioning to a degree, thus bringing the arch slots of the brackets generally closer into alignment. The force requirements of an archwire at midtreatment are therefore different than at the beginning of treatment. The same general level of physiologically-corrective forces must be transferred to the teeth even though the deflection angles of the wire will have decreased. In other words, at mid-treatment, a wire exhibiting a moderate spring rate when moderately deflected is required.

At the end of treatment, the teeth, brackets and arch slots will fall much closer into a final alignment. In order to maintain the corrective force levels within a physiologically-effective range, such an archwire must have a very rapid spring rate at low deflections.

To accommodate this wide range of resilience needed over the span of treatment, orthodontists use archwires that vary in terms of physical dimensions, alloy and temper and even physical or metallurgical composition. An orthodontist may begin treatment with highly flexible archwires such as 0.012 or 0.014 in. round stainless steel with a relatively low tensile strength of about 125,000 PSI for example. Such wires may exhibit a modulus of elasticity (Young's modulus) of about 8,000,000 to 10,000,000. Woven wires consisting of multiple strands of smaller individual wires have also proven capable of handling the extreme contortions and twists encountered at the beginning of treatment, while delivering physiologically-appropriate corrective forces. During the finishing stage however, orthodontists use what are termed "finishing wires" that are formed from near spring-temper, work-hardened stainless steel or heat-treated cobalt-chromium alloys. Finishing wires typically exhibit a tensile strength approaching 300,000 PSI, with corresponding hardness. Such wires are provided in rectangular cross-sections to fully exploit Edgewise mechanics. The dimensions of such rectangular finishing wires completely fill the rectangular arch slot so that in addition to the material being harder and stiffer, there is more cross-sectional area of material contributing to force generation. In terms of modulus of elasticity (Young's modulus), very flexible archwires used at the beginning of treatment may exhibit a modulus as low as 8,000,000. Whereas at the other extreme, very rigid finishing wires may exhibit a modulus of over 31,000,000.

From the historical perspective, in the late 1800's, orthodontic wire was first formed from precious metals such as palladium, gold and platinum. Stainless steel was introduced to dentistry in the early 1930's. Due to the wide range to which stainless can be work hardened and its other desirable qualities, stainless steel has almost entirely replaced precious metals in dentistry.

In the early 1960's a remarkable alloy consisting of about 55% nickel and 45% titanium by weight was developed as a product of military research. Given the name Nitinol, it held great promise for meeting the long-sought orthodontic objective of achieving very light and gentle forces at very high deflection angles. Nitinol is in fact very gentle. In comparable shapes and in terms of its modulus of stiffness, Nitinol is only about 25% as stiff as equally-sized standard orthodontic stainless steel wire. Other unique properties of Nitinol involve its extraordinarily gentle spring rate. In particular, Nitinol demonstrates a unique loading plateau known as super elasticity. After moderate deflection, further deflection generates very little additional force. Nitinol's nearly flat super elastic stress/strain trait is maintained through a very wide range of deflection. Such properties are seen as ideal for delivering the gentle, continuous forces needed in orthodontics.

When first introduced to orthodontics, Nitinol quickly became appreciated as being perhaps the ultimate orthodontic wire because of its combination of remarkably desirable force characteristics. A refined version of the material was developed for orthodontic use and its very desirable properties provided the basis for successful commercialization. Today, Nitinol has been utilized in the fabrication of nearly every type of orthodontic energy-storing spring device. U.S. Pat. No. 4,037,324 to Andreason describes basic methodologies for integrating Nitinol into orthodontic treatment. A technical discussion of the unusual metallurgical properties of Nitinol is presented by Garrec et al., "Stiffness in Bending of a Superelastic Ni—Ti Orthodontic Wire as a Function of Cross-Sectional Dimension," *The Angle Orthodontist*, vol. 74, no. 5, pp. 691-696 (2003), which is incorporated herein by reference.

Regardless of temper and metallurgical composition, all low spring-rate wires used in orthodontics, including Nitinol, share the property of being very flexible and at the same time, resistant to yielding (taking a set) unless very high deflection angles are attempted. Due to the extreme flexibility of these wires, orthodontists usually do not attempt to install activations or corrective adjustment bends in such wires. The highly flexible wires used early in treatment can have either a round or rectangular cross-section. Nitinol wires are commercially available in a rectangular cross-section, including full-sized slot-filling configurations. Using such wires allows practitioners to use such wires in an Edgewise mechanics-mode. This means that correction in terms of torque can be desirably pursued from the start of treatment. Again, very flexible early phase wires are usually relegated to initial unscrambling and leveling of a malocclusion, which involve relatively large movements separate from aesthetic positioning considerations later in treatment. Achieving torque objectives, even from the earliest point in treatment, has however proven advantageous.

Returning to the earlier discussion of Edgewise mechanics, a more detailed description of current and historical practice will serve to highlight the utility of the present invention. Today, commercially-available bracket systems consist of brackets where the orientation of the arch slot is optimized on a tooth-by-tooth basis to reflect the ideal aesthetic positioning of each tooth. In the past however, Edgewise mechanics was first employed using brackets that were all identical. No such tooth-by-tooth bio-engineered features were incorporated into bracket fabrication prior to the early 1970's. Early orthodontists were required to form highly detailed archwires in order to impart the corrective forces and orientations needed by each tooth. To do that, orthodontists used special pliers and torqueing wrenches to install specific types of bends in short segments of the archwire corresponding to the location of the bracket's arch slots. Those bends were referred to as first, second and third-order bends, and those bends are described below:

First-Order Bends. First-order bends involved a direct outstep or in-step of the archwire. Such a bend would establish the prominence of a tooth. An example of prominence can be seen in maxillary lateral incisors. Maxillary lateral incisors function best when inset slightly relative to the central incisors and the cuspids. In aesthetic terms, without the insetting of upper lateral incisors, a patient's smile may appear unnatural. Upper and lower cuspids however are properly positioned in terms of prominence when outset. To place a first order bend in an archwire, an orthodontist would form a sharp inward-stepping zig-zag bend followed by another bend in reverse, stepping back out to the pre-established natural curve of the archwire. Such an in-step bend may be required to either outset the cuspids or inset the lateral incisors.

Second-Order Bends. Second-order bends are best described by looking directly at the facial surface of a tooth's crown and imagining its center point. Second order bends involve clock-wise or counter clockwise rotation of the tooth about that point (i.e., rotation about a horizontal axis passing perpendicular to the enamel and through this center point of a tooth). It can be said that each tooth has a statistically normal angle in this sense, generally called angulation. To place a second order bend in a wire, an orthodontist would install an uphill or downhill cant, followed by a returning set of bends back to the wire's predetermined form.

Third-Order Bends. Third-order bends involve the installation of short torsional bends where the torsioned segment is intended to inter-work with the rectangular slot walls and floor to swing the root of the tooth inward or outward. This was discussed earlier as the central attribute of Edgewise mechanics. To install a third-order bend, an orthodontist would place torqueing wrenches in the area to be torqued and on an adjacent segment and install the bend through torsion. A returning bend at the other end of the slot-engaging segment would return the wire to a zero torque value and its predetermined shape.

Today, even with extensively bioengineered brackets, orthodontists often need to install first, second and third-order bends in order to compensate for some error in their positioning of brackets when the brackets were originally bonded to the teeth. Another reason to resort to such bends is to over-activate or further bias an archwire against stubborn teeth that are slow to respond to standard force levels.

Yet other reasons exist for returning to the practice of installing first, second or third-order bends. U.S. Pat. No. 5,080,584 (Karabin) and U.S. Pat. No. 6,036,489 (Brosius) both teach the use of low-rate, high-deflection orthodontic wire of the type typically used at the beginning of orthodontic treatment. In both patents however, the wire is disclosed as having been formed into a rectangular cross-section. In other words, in addition to the unscrambling and leveling functions envisioned for their low-rate wires, the intent of these inventors is to also begin correction in terms of torque from the start of treatment. Beginning efforts toward achieving torque objectives at such an early point in treatment can shorten the overall duration of treatment and reduce the tendency for relapse of the teeth post treatment. Rectangular, first-phase archwires disclosed by the Karabin and Brosius patents have become popular.

Again, both Karabin and Brosius contemplate low-rate wires. Brosius in particular considers the application of super-elastic Nitinol as an Edgewise energy-storing device. To place such a consideration into perspective, it can be said that indeed, since the early 1980s, Nitinol wire products have proven to be extremely successful in the orthodontic applications, but with one significant limitation. Nitinol wire, in its ideal super-elastic condition is extremely hard to bend. Placing bends in super-elastic Nitinol requires extreme over-bending in order to cause the wire to yield sufficiently to accept deformation. This difficulty in forming sharp bends in Nitinol-type wire has been lamented as the one shortfall of Ni—Ti wire in orthodontic applications. The present invention directly addresses this shortcoming. In the broader perspective, all types of first-phase, low-rate wires share the same attribute of requiring large degrees of over-bending in order to accept a sharp bend feature. Woven wire will not accept an enduring bend at all. To illustrate the need for over-bending, a bend of 90 degrees as typically sought for archwires in many treatment situations. This can require extreme over-bending to the extent that the wire can double back and contact itself. This sort of interference causes a fixturing problem that is hard to accommodate using standard dental pliers at chairside. Further, it requires the bending to occur in an out-of-axis manner, resulting in a slight helical distortion.

Prior Art Pliers. Traditional orthodontic wire-bending pliers became standardized in both configuration and methods of use prior to the advent of the titanium-based low-rate wire alloys commonly used today. As a group, they are not capable of accomplishing any significant degree of over-bending, in contrast to the present invention. Pliers designed in the past were able to adequately form sharp bends in stainless steel wires, but are generally incapable of forming sharp bends in fully elastic Ni—Ti wire for example.

Another problem is presented by interference between the beaks of the pliers. For example, consider the wire-forming surfaces 35 and 45 of the beaks 30, 40 of the pliers 20 in FIG. 1 that over-bend the wire by more than 90 degrees. As the beaks 30, 40 are closed, there comes a point where the two wire-forming surfaces 35, 45 have a proximity to each other that is less than the effective wire dimension or diameter. With a conventional pliers hinge, this would result in an interfering relationship between the two beaks 30, 40 with the wire 10 between these wire-forming surfaces 35, 45. Now, a small interference (e.g., 0.005 in. or less) may be accommodated given some play in the structure of the hinge components of the pliers, or by some shared lateral flexing of the beaks. The combined lateral flexing of the beaks required in the current example of 0.005 in. may well be tolerated, but some scuffing of the upper and lower faces of the wire may occur. The problems that are encountered as higher over-bend angles are incorporated into the beaks are that the degree of scuffing of the wire, and the amount of give or flexing required of the beaks becomes unworkably excessive. For example, excessive scuffing of the wire can actually shear-off material and significantly scar the wire. Such blemishes are to be avoided in orthodontic wire because they often lead to breakage. Outward flexing of the pliers' beaks can also lead to rapid wear of the hinge and excessive flexing of the beaks can lead to embrittlement and breakage.

Solution to the Problem. The present invention provides pliers to accommodate the high degree of spring-back encountered when attempting to form controlled bends in low-rate orthodontic wire. In particular, the pliers include a hinge and spring that allow a range of lateral motion between the beaks of the pliers (i.e., relative motion parallel to the axis of the hinge) sufficient to prevent interference between the wire-forming surfaces of the beaks.

SUMMARY OF THE INVENTION

This invention provides pliers for forming orthodontic wires having opposing beaks with complementary wire-forming surfaces that include interfering portions. A hinge mechanism enables the beaks to open and close by rotating about an axis, and also allows a range of axial motion between the beaks sufficient to prevent interference between the wire-forming surfaces as the beaks are closed. A spring, such as a Belleville washer, exerts a biasing force parallel to the hinge axis to maintain alignment of the beaks, but allows the required range of axial motion between the beaks to prevent interference.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 6 is a perspective view of a Belleville washer 50.

FIG. 7 is another perspective view of a Belleville washer 50.

FIG. 8 is a perspective view of stacked series of Belleville washers.

FIG. 13a is a vertical cross-sectional view of the hinge of the pliers with the outer Belleville washers 50 uncompressed.

FIG. 13b is a corresponding vertical cross-sectional view of the hinge of the pliers with the outer Belleville washers 50 compressed to allow a range of lateral motion between the beaks 30, 40.

FIGS. 14a-14c are a series of vertical cross-sectional views of the camming mechanism in the embodiment of the pliers appearing in FIGS. 5, 10 and 11 as the beaks of the pliers close.

DETAILED DESCRIPTION OF THE INVENTION

Figure 1:
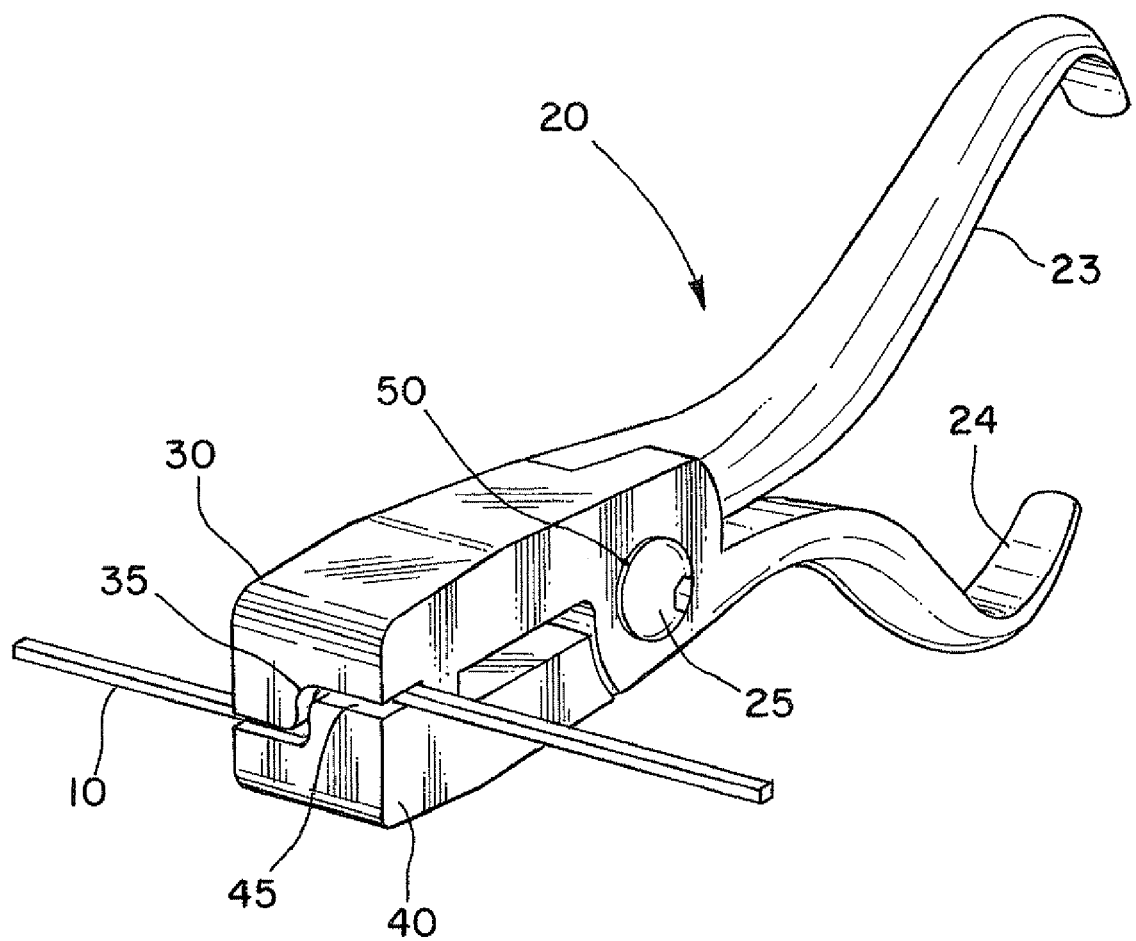
FIG. 1 is a front perspective view of pliers 20 implementing the present invention.
Figure 2:
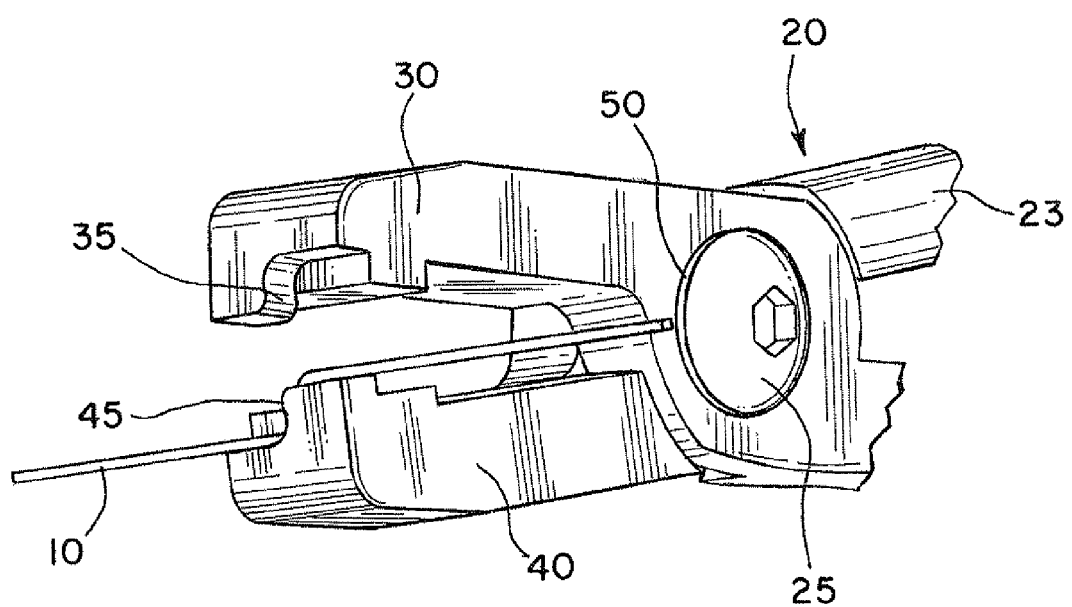
FIG. 2 is a detail perspective view of the pliers 20 and a formed wire 10, with the beaks 30, 40 of the pliers 20 in an open position.
Figure 3:
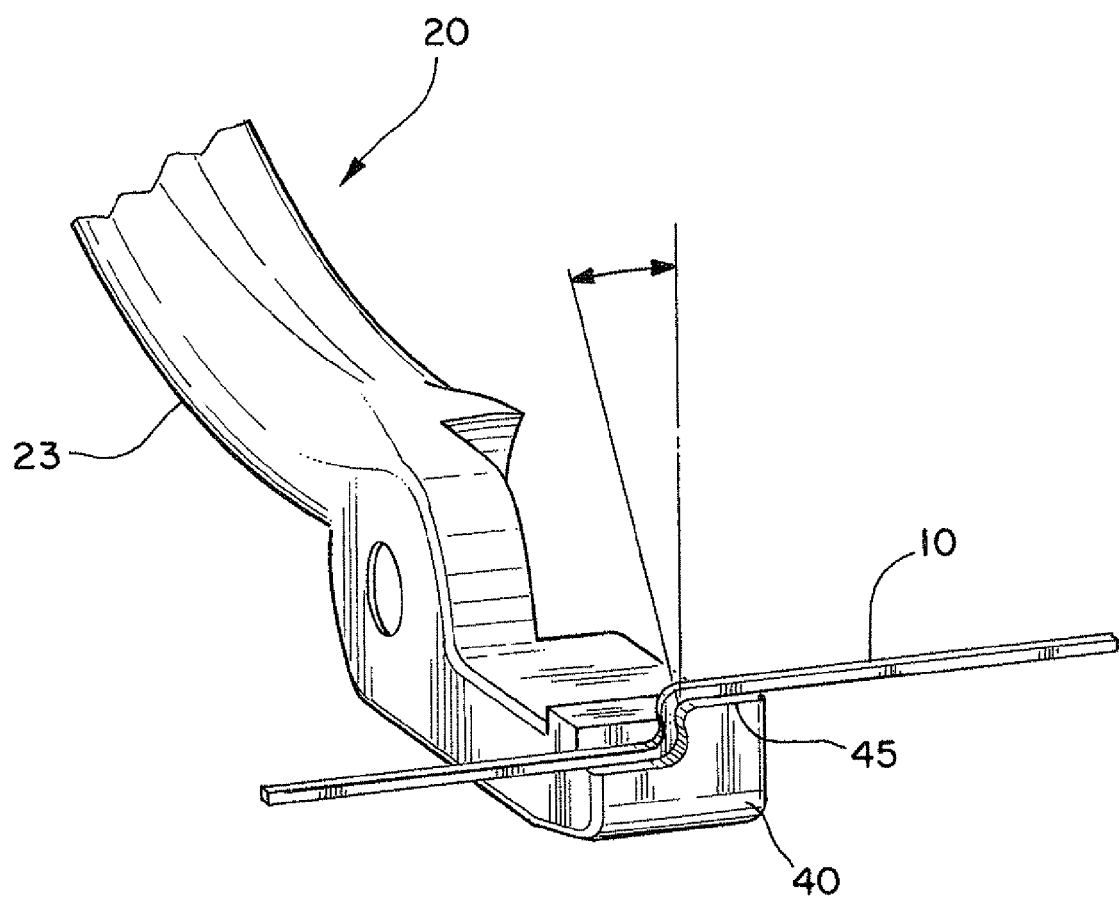
FIG. 3 is a detail perspective view of one beak 40 of the pliers 20 and the formed wire 10.
Figure 4:
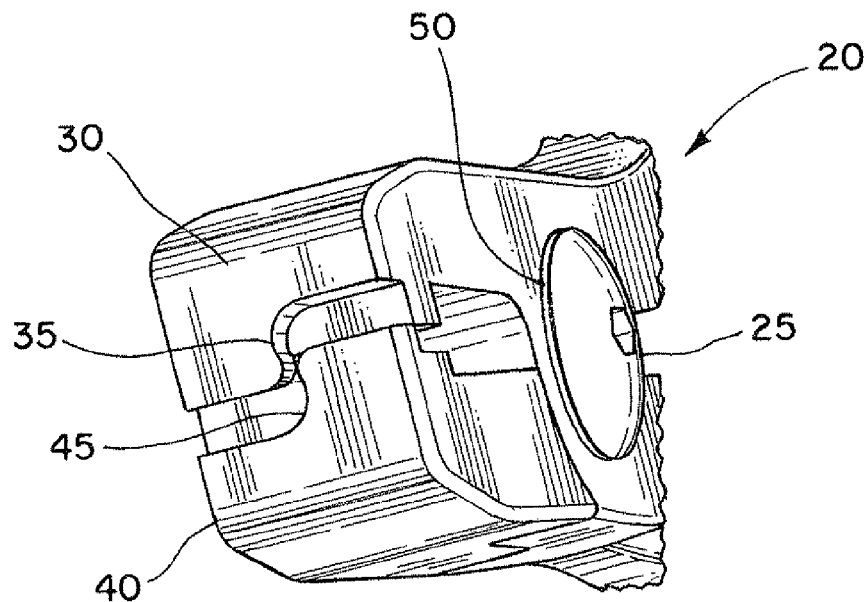
FIG. 4 is a detail perspective view of the pliers 20 with the beaks 30, 40 partially closed.

One embodiment of the present invention is shown in FIGS. 1-4. FIG. 1 is a front perspective view of the pliers 20. FIG. 2 is a detail perspective view with the beaks of the pliers 20 in an open position. FIG. 3 is a detail perspective view of lower beak 40 of the pliers and the formed wire 10. FIG. 4 is a detail perspective view of the pliers 20 with the beaks 30, 40 partially closed. The major components of the pliers 20 are two handles 23, 24 and beaks 30, 40 rotatably connected by a hinge mechanism 25. Each beak 30, 40 can be formed as a single piece with one of the handles 23, 24, as is the case with many conventional pliers.

The beaks 30, 40 include complementary wire-forming surfaces 35, 45 for forming an orthodontic wire into a predetermined shape. As the pliers 20 are closed, the wire-forming surfaces 35, 45 are brought together to form a channel having the desired shape and dimensions to form a wire. The spacing between the wire-forming surfaces 35, 45 should also be selected to grip the wire without excessive scuffing, and therefore should roughly match the wire dimension or diameter.

The hinge 25 allows rotation of the handles 23, 24 and beaks 30, 40 about an axis over a range of angular positions to open and close the beaks 30, 40 when the handles 23, 24 are manually actuated. The hinge 25 can include a pin that is threaded into one of the handles 23 or 24 and has a generally cylindrical barrel that fits through a hole in the second handle and allows rotation of the second handle with respect to the hinge pin. An enlarged head on the end of the hinge pin retains the second handle on the cylindrical barrel of the hinge pin. Alternatively, the hinge pin can extend through aligned holes in both handles 23, 24. In this configuration, a nut is threaded onto one end of the hinge pin. The handles 23, 24 are retained between the nut and the enlarged head of the hinge pin.

In the present invention, the hinge allows a range of relative movement between the beaks 30, 40 parallel to the hinge axis. In addition, the present invention includes a number of springs 50 and 55 that exert biasing forces parallel to the axis of the hinge 25 to maintain alignment of the beaks 30 and 40, but allows the range of axial motion (i.e., lateral motion or excursion) between the beaks 30 and 40 sufficient to prevent interference between the wire-forming surfaces 35, 45 of the beaks 30, 40 as they are opened or closed. For example, the configuration of the channel between the wire-forming surfaces 35, 45 in the embodiment of the pliers shown in FIGS. 1-4 allows a small degree of over-bending of the wire 10 (past 90 degrees) and thus counteracts the spring-back potential of low-rate wire.

Any of a wide variety of conventional springs can be employed to load the hinge pin 25 to provide a biasing force while allowing a range of relative movement between the beaks 30, 40 parallel to the hinge axis. This lateral excursion of the beaks avoids the problems of wear and damaging stresses to the pliers and undesirable scuffing of the wire as described earlier. Lateral or axial movement of the beaks 30, 40 acts to compress the springs 50, 55, and as the beaks 30, 40 move to their fully-closed position, the springs 50, 55 bias the beaks 30, 40 to return to a coplanar alignment (i.e., without significant lateral or axial excursion) in the fully closed position.

Preferably, the springs 50, 55 consist of a number of Belleville washers. An example of a Belleville washer is depicted in more detail in the perspective views provided in FIGS. 6 and 7. Belleville washers are commercially available in a range of alloys including spring-temper stainless steel. For the purposes of this application, the term "Belleville washer" should be broadly interpreted to cover any type of washer having a generally frusto-conical shape or cupped shape that is suitable for exerting a spring force.

An individual washer of this type can serve as a very high rate spring, or multiple washers may be stacked in alternating orientation to reduce the rate of a composite spring. Such a configuration is contemplated for the current invention and shown in FIG. 8. In contrast, stacking a plurality of Belleville washers in the same direction will add the spring constant in parallel, creating a stiffer spring assembly (with the same deflection). Mixing and matching directions allow a desired spring constant and deflection capacity to be designed. All such pèrmutations and combinations of washers can be employed in the present invention In addition, Belleville washers can be combined with other types of springs in the present invention.

A tight and stiff compression spring could serve to load the hinge pin 25 to provide a biasing force while allowing a range of relative motion between the beaks 30, 40. These springs are sometimes called "die springs." However, such a spring would tend to introduce greater bulk to the pliers.

Figure 3A:
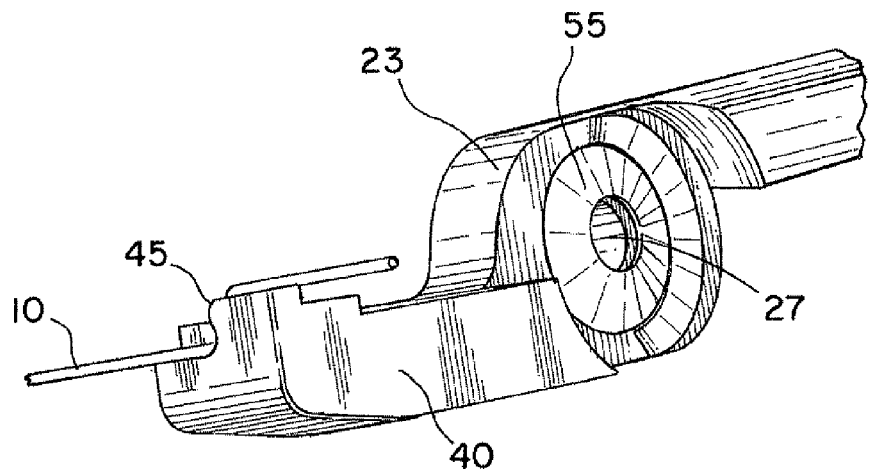
FIG. 3*a* is a detail perspective view showing the other side of the beak 40 of the pliers 20 in FIG. 3.
Figure 3B:
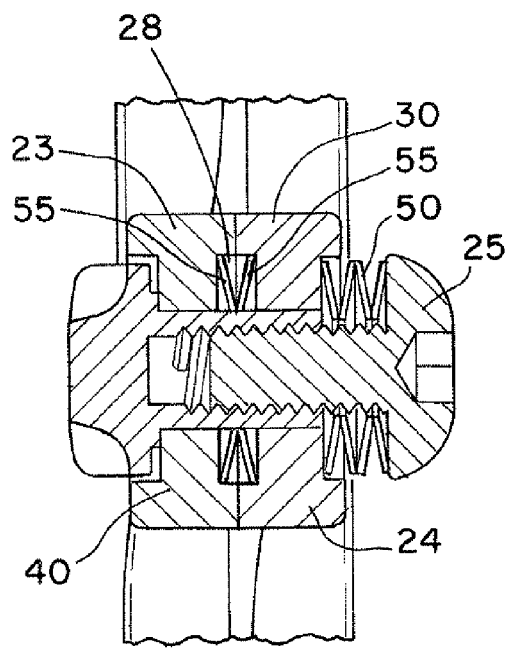
FIG. 3*b* is a vertical cross-sectional view of the pliers 20 taken through the hinge pin 25.
Figure 3C:
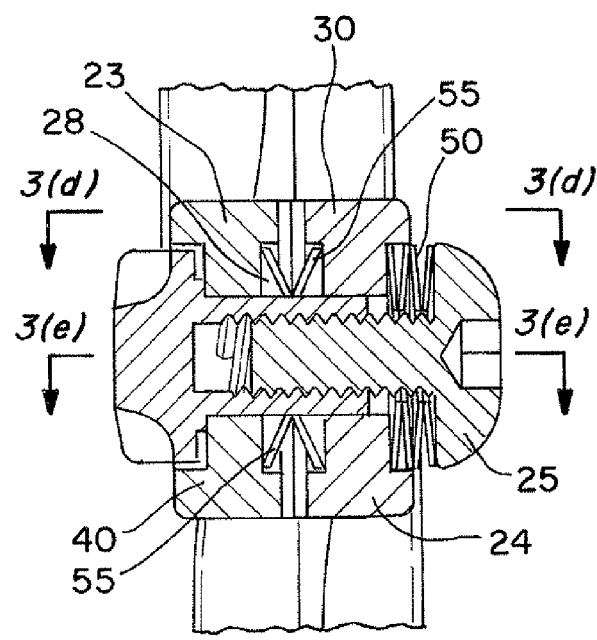
FIG. 3*c* is a vertical cross-sectional view corresponding to FIG. 3*b* showing lateral excursion of the hinge assembly as the pliers pass through the region of interference between the beaks.

The embodiment of the pliers 20 shown in FIGS. 1 and 3c includes two separate springs 50 and 55. The first or outer spring 50 is a Belleville washer on the hinge pin 25 that is compressed between the head of the hinge pin 25 and the exterior surface of one of the beaks 30. This outer spring 50 exerts a biasing force along the hinge axis that tends to compress the beaks 30, 40 together, so that the beaks tend to maintain proper alignment with respect to one another, particularly in the closed position. But, the outer spring 50 also allows a range of lateral excursion between the beaks 30, 40 as the pliers 20 open or close.

Figure 3D:
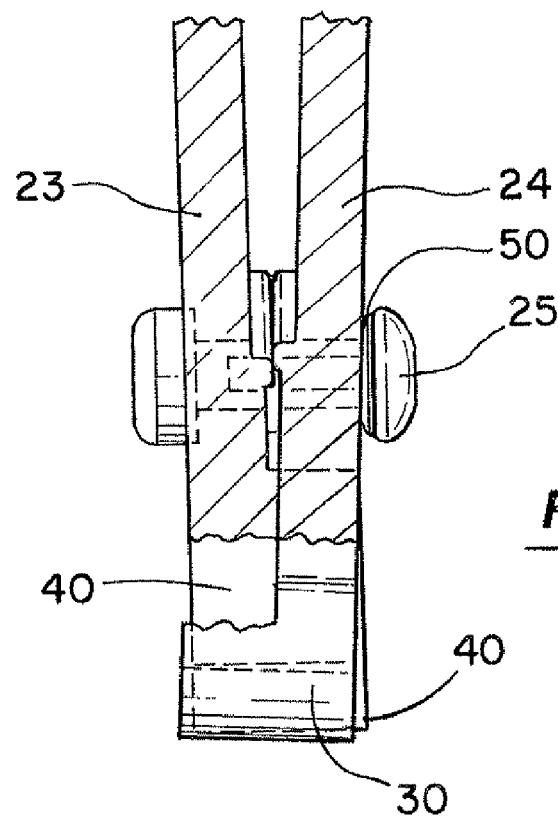
FIG. 3*d* is a top view of the pliers showing inward lateral excursion of the beaks 30, 40 as the pliers pass through the region of interference between the beaks.
Figure 3E:
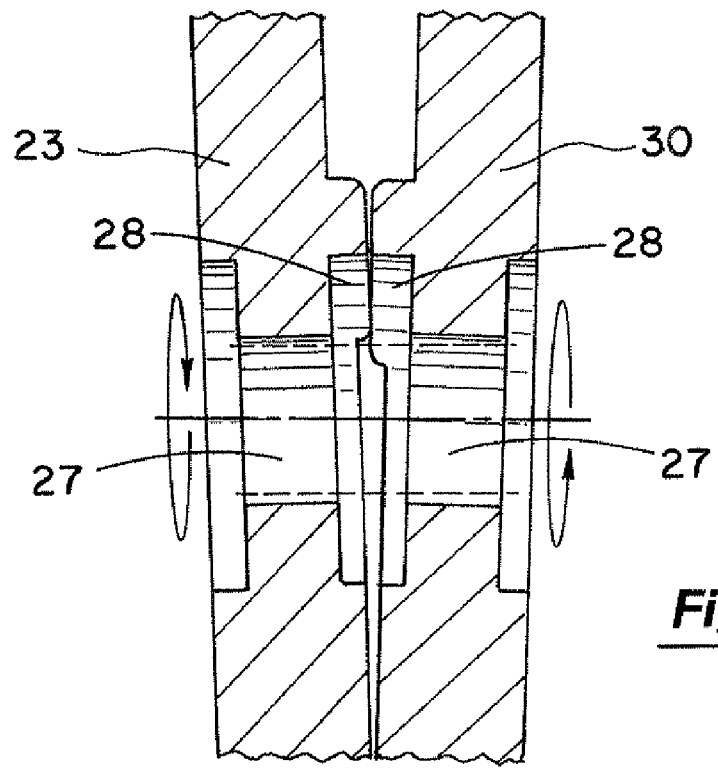
FIG. 3*e* is a detail cross-sectional view of the hinge portion of the beaks 30, 40 with the hinge pin removed to show non-parallel movement of the beaks as the pliers pass through the region of interference between the beaks.

In contrast, the second or inner spring 55 is a Belleville washer on the hinge pin 25 that is held in annular recesses 28 between the beaks 30, 40. This is illustrated in the cross-sectional view provided in FIGS. 3b, 3c and 3e. The inner spring 55 is also shown in FIG. 3a. The inner spring 55 exerts a biasing force along the hinge axis that tends to separate the beaks 30, 40, and thereby allows a range of lateral excursion of the beaks 30, 40. The diameter of the hinge pin 25 may be slightly undersized with respect to the holes 27 through beaks 30, 40 to allow a degree of non-parallel movement between the beaks 30, 40 as they open or close, as shown in FIGS. 3d and 3e. This non-parallel movement may be necessary to prevent mechanical interference between the wire-forming surfaces 35, 45 of the beaks 30, 40 as the pliers 20 open or close.

Figure 5:
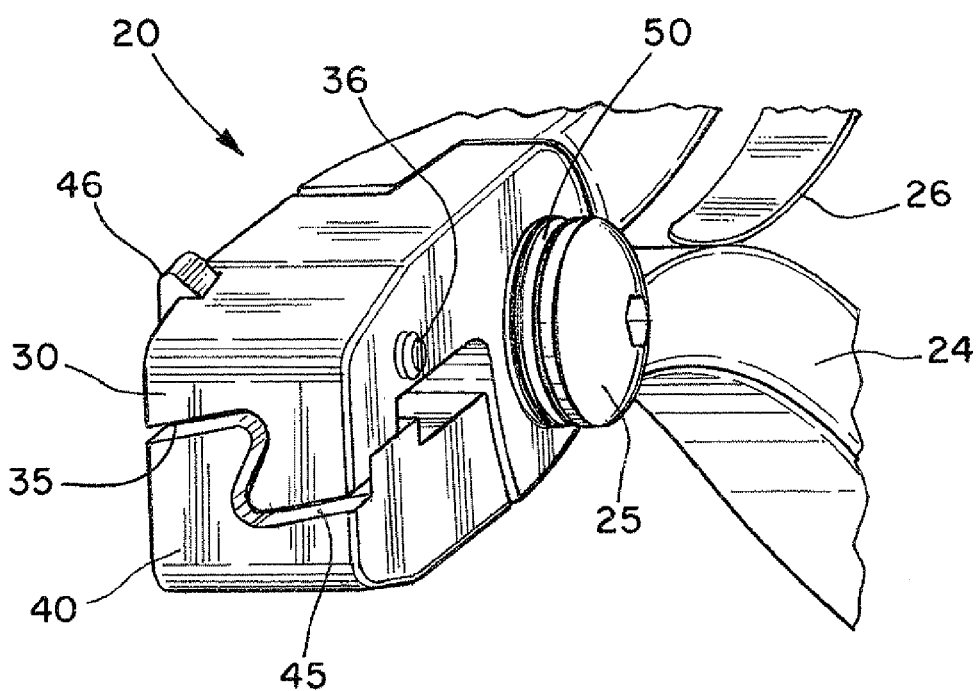
FIG. 5 is a detail front perspective view of another embodiment of the pliers 20 with a camming mechanism to guide lateral motion of the beaks 30, 40.

Another embodiment of the current invention is depicted in FIG. 5 having higher over-bend angles. Compared to the first embodiment disclosed in FIGS. 1-4, the reader can see that the over-bend angles shown in FIG. 5 are more acute. Portions of the wire-forming surfaces 35, 45 that were horizontal in the first embodiment can be canted to increase the over-bend angle even further. The embodiment depicted in FIG. 5 has a beak configuration that achieves about 52 degrees of over-bend. As can be seen in FIG. 5, if the pliers employed a conventional hinge, the beaks would mechanically interfere with each other to the extent that once closed, they could not open or once opened they could not close.

Figure 9:
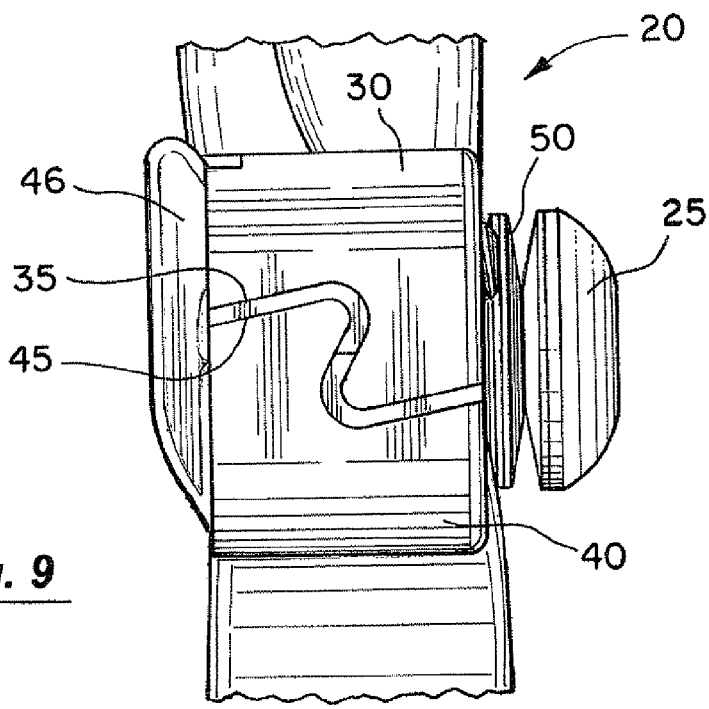
FIG. 9 is a front view of the embodiment of the pliers 20 shown in FIG. 5.
Figure 10:
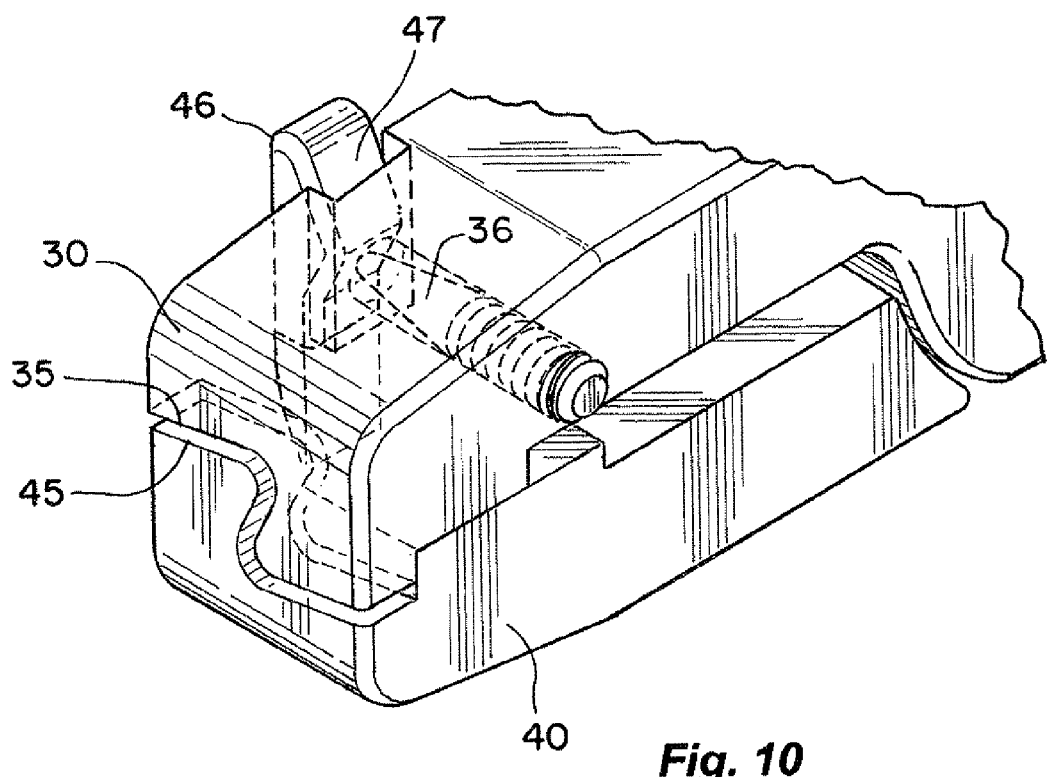
FIG. 10 is a detail perspective view of the beaks 30, 40 of the pliers 20 depicted in FIGS. 5 and 10, with the camming mechanism shown in dashed lines.
Figure 11:
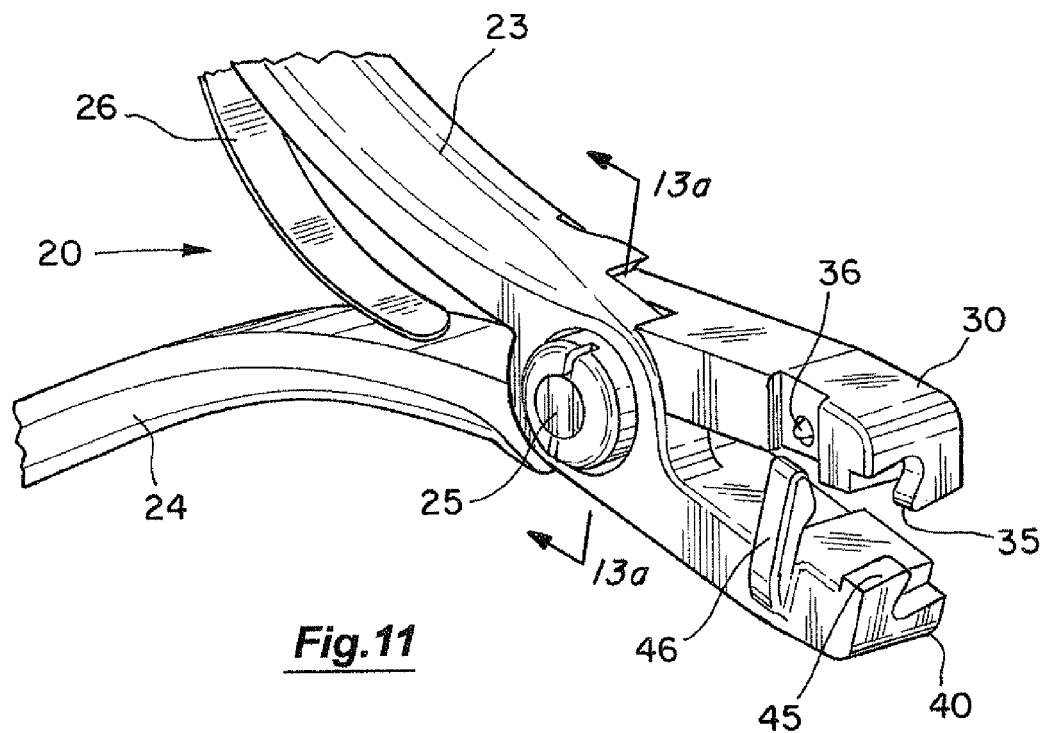
FIG. 11 is a detail perspective view of the embodiment of the pliers 20 from FIGS. 5 and 10 with the beaks 30, 40 open.
Figure 12:
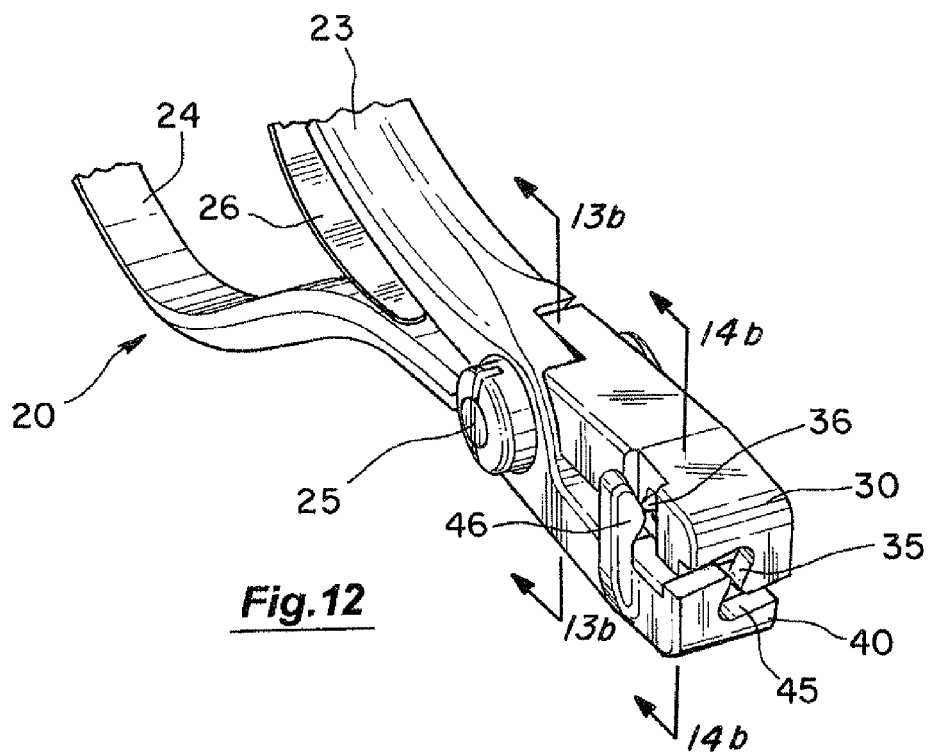
FIG. 12 is a detail perspective view of the embodiment of the pliers 20 from FIGS. 5, 10 and 11 with the beaks 30, 40 partially closed.

The embodiment of the present invention shown in FIGS. 5 and 9-14c combines spring-loaded resistance to lateral excursion of the beaks with additional features that produce a camming action that guides the lateral motion of the beaks 30, 40 over the course of opening/closing the pliers. In particular, the camming action moves the beaks 30, 40 apart parallel to the axis of the hinge pin 25 over the interference point when an orthodontic wire 10 is positioned between the beaks 30, 40. FIG. 10 is a detail perspective view of the beaks of the pliers depicted in FIGS. 5 and 10, with the camming mechanism shown in dashed lines. FIG. 11 is a detail perspective view of the embodiment of the pliers from FIGS. 5 and 10 with the beaks open. FIG. 12 is a detail perspective view of the pliers with the beaks 30, 40 partially closed.

As shown in these figures, a round-nose cam follower 36 on the upper beak 30 of the pliers has a hardened, adjustable point that rides on the contoured camming surface 47 of the standing cam arm 46 extending from the lower beak 40. The cam follower 36 is adjustably installed with threads in the upper beak 30 as shown in FIG. 10. The inherent interference problem encountered if the pliers is configured for high degrees of over-bend is solved by the camming relationship between the camming surface 47 and the cam follower 36. These features allow temporary lateral excursion of the beaks 30, 40 for significant clearance, which is accommodated through the give provided by the Belleville washers 50, 55. Once the cam follower 36 passes over the high point of the standing cam 47, the wire-forming surfaces 35, 45 of the upper and lower beaks 30, 40 fall back into a parallel relationship due to the spring-loading of the Belleville washers 50, 55 as they push the beaks 30, 40 into alignment. This is depicted in the series of vertical cross-sectional views of the camming mechanism shown in FIGS. 14a-14c.

The cam follower 36 and the standing cam 47 may be incorporated in a reversed configuration so that the beaks 30 and 40 are deflected inward as the beaks pass the high point. Such a configuration may also serve, along with leaf spring 26 to allow the pliers to be opened easier after a wire-forming step is completed. Since some wire-forming steps are accomplished by an orthodontist at chairside with the wire in place in a patient's mouth, the pliers need to open easily after forming an archwire using a pinky finger, for example. Multiple sets of cams and standing cams may be incorporated to facilitate both wire forming and ease of opening.

FIG. 13a is a vertical cross-sectional view of the hinge 25 of the pliers with the outer Belleville washers 50 relatively uncompressed. FIG. 13b is a corresponding vertical cross-sectional view of the hinge 25 with the outer Belleville washers 50 compressed to allow a range of lateral or axial motion between the beaks 30 and 40.

Optionally, the pliers 20 can include a leaf spring 26 between the handles 23 and 24, as shown in FIGS. 11 and 12, to bias the pliers in the open position, and to assist in reopening the pliers from the closed position. As previously discussed, while the beaks 30, 40 are pivoting toward the closed position, the cam follower 36 rides on the cam surface 47 and causes the beaks to deflect laterally over their region of interference. However, after the bends have been formed in the wire and the pliers are released, a reversal of the closing sequence is required to open the beaks. In other words, opening the pliers after use requires the cam follower 36 to again ride on the cam surface 47 past its apex. For the user, the requirement of having to grasp the handles and pull them apart after each use can be awkward and might pose a distraction. The force exerted by the leaf spring 26 helps to overcome the resistive forces in moving the cam follower 36 back over the cam surface 47 to the open position.

It should be understood that other types of camming mechanisms could be substituted. For example, the camming surface could be implemented as a surface radially surrounding the hinge pin. Alternatively, complementary arcuate camming surfaces can arranged in a radial pattern around the hinge pin on both beaks.

One possible concern might be that Belleville washers 50 might not impart adequate closing forces to the beaks 30, 40 to push the wire-forming surfaces 35, 45 into a tight complementary relationship to properly form the wire 10. That concern is ameliorated by an examination of the complementary relationship of the wire-forming surfaces 35, 45 as shown in the front view of the pliers illustrated in FIG. 9. FIG. 9 depicts the pliers 20 in the closed or forming position, assuming that a user is squeezing the handles 23, 24 of the pliers. The beaks 30, 40 are in direct apposition to each other with considerable force. The lower beak's force in this view is directed generally upward and the upper beak's force is directed generally downward. Due to the slanted portions of the wire-forming surfaces 35 and 45, however, there are components to the compressive forces exerted by the beaks 30, 40 that tend to slide the beaks 30, 40 together parallel to the hinge axis), and thereby reduce lateral excursion of the beaks 30, 40. This lateral clamping of the beaks, or tendency to nest in concentric relation is an inherent advantage, and can serve to counter any lateral weakness resulting from the use of Belleville washers.

It should be noted that the present invention can be implemented in a wide variety of pliers to produce a variety of bends. This may best be implemented by a plurality of pliers, each of which is optimized for a specific type of bend, wire diameter and wire alloy. It should also be noted that orthodontists often need to create features in a wire that incorporate more than one bend. Thus, multiple pliers may be required to form the various bends required for a single feature. For example, orthodontists often need to form a pair of zig-zag shaped bends for forming a jog in an archwire. One example of this is shown by the shape of the wire 10 in FIG. 3. It should be understood that such bends can either jog the wire upward or downward. In many cases, it is possible to form either an upward or downward jog with the same pliers by approaching the wire from its lingual or labial/buccal aspects. Alternatively, separate pliers can be designed for upward jogs and downward jogs. These pliers would essentially be mirror images of each other.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:
1. A pliers for forming orthodontic wires comprising:
a first beak having a wire-forming surface;
an opposing second beak having a complementary wire-forming surface, wherein the wire-forming surfaces of the beaks have interfering portions, so that the beaks would mechanically interfere with each other on opening and closing;

a hinge enabling the beaks to open and close by rotating about an axis, and allowing a range of axial motion between the beaks sufficient to prevent interference between the wire-forming surfaces as the beaks are closed; and at least one spring exerting a biasing force along the axis to maintain alignment of the beaks, but allowing the range of axial motion between the beaks; wherein the interfering portions are configured such that the beaks would be prevented from opening and closing without the range of axial motion allowed by the at least one spring.

2. The pliers of claim 1 wherein the spring comprises a Belleville washer.

3. The pliers of claim 1 wherein the spring comprises a stacked plurality of Belleville washers.

4. The pliers of claim 1 wherein the hinge comprises hinge pin.

5. The pliers of claim 1 wherein the at least one spring comprises:
a first spring exerting a biasing force to maintain alignment of the beaks; and
a second spring between the beaks allowing the range of axial motion between the beaks.

6. The pliers of claim 1 further comprising a camming surface guiding axial motion of the beaks as the pliers close.

7. The pliers of claim 1 wherein the wire-forming surfaces form a channel of a predetermined shape for forming a wire with the pliers in a closed position.

8. The pliers of claim 7 wherein the wire-forming surfaces form a channel having a bend greater than 90 degrees.

9. The pliers of claim 7 wherein the wire-forming surfaces are spaced apart from one another by a distance selected to match a predetermined wire dimension.

10. A pliers for forming orthodontic wires comprising:
a first beak having a wire-forming surface;
an opposing second beak having a complementary wire-forming surface, wherein the wire-forming surfaces of the beaks have interfering portions, so that the beaks would mechanically interfere with each other on opening and closing;
a hinge pin enabling the beaks to open and close by rotating about the axis of the hinge pin, and allowing a range of axial motion along the hinge pin between the beaks sufficient to prevent interference between the wire-forming surfaces as the beaks are closed; and
at least one Belleville washer on the hinge pin exerting a biasing force along the axis of the hinge pin to maintain alignment of the beaks, but allowing the range of axial motion between the beaks; wherein the interfering portions are configured such that the beaks would be prevented from opening and closing without the range of axial motion allowed by the at least one Belleville washer.

11. The pliers of claim 10 further comprising a stacked plurality of Belleville washers on the hinge pin.

12. The pliers of claim 10 wherein the at least one Belleville washer comprises:
a first Belleville washer exerting a biasing force to maintain alignment of the beaks; and
a second Belleville washer between the beaks allowing the range of axial motion between the beaks.

13. The pliers of claim 10 wherein the wire-forming surfaces form a channel of a predetermined shape for forming a wire with the pliers in a closed position.

14. The pliers of claim 10 further comprising a camming surface guiding axial motion of the beaks as the pliers close.

15. The pliers of claim 10 further comprising
a contoured camming surface on the first beak; and
a cam follower on the second beak contacting the camming surface to guide axial motion between the beaks as the beaks are closed and thereby prevent interference between the wire-forming surfaces.

16. A pliers for forming orthodontic wires comprising:
a first beak having a wire-forming surface;
an opposing second beak having a complementary wire-forming surface, wherein the wire-forming surfaces of the beaks have interfering portions, so that the beaks would mechanically interfere with each other on opening and closing;
a hinge enabling the beaks to open and close by rotating about an axis, and allowing a range of axial motion between the beaks sufficient to prevent interference between the wire-forming surfaces as the beaks are closed;
a spring exerting a biasing force along the hinge axis to maintain alignment of the beaks, but allowing the range of axial motion between the beaks; wherein the interfering portions are configured such that the beaks would be prevented from opening and closing without the range of axial motion allowed by the spring and
a contoured camming surface on the first beak;
a cam follower on the second beak contacting the camming surface to guide axial motion between the beaks as the beaks are closed and thereby prevent interference between the wire-forming surfaces.

17. The pliers of claim 16 wherein the hinge comprises a hinge pin.

18. The pliers of claim 17 wherein the spring comprises at least one Belleville washer on the hinge pin.

* * * * *